United States Patent [19]

Williams

[11] Patent Number: 5,709,675

[45] Date of Patent: Jan. 20, 1998

[54] SMOKE REDUCING DEVICE FOR MINIMALLY INVASIVE SURGERY

[75] Inventor: Ronald A. Williams, Grand Rapids, Mich.

[73] Assignee: Medtronic, Inc., Minneapolis, Minn.

[21] Appl. No.: 637,070

[22] Filed: Apr. 24, 1996

[51] Int. Cl.$^6$ .................................................. A61B 17/20
[52] U.S. Cl. .............................. 606/1; 606/41; 606/49; 604/22; 604/35
[58] Field of Search .................... 606/32–34, 37–42, 606/45–50, 1; 604/21, 22, 35

[56] References Cited

U.S. PATENT DOCUMENTS

| | | |
|---|---|---|
| 4,562,838 | 1/1986 | Walker . |
| 5,055,100 | 10/1991 | Olsen . |
| 5,246,440 | 9/1993 | Van Noord . |
| 5,342,349 | 8/1994 | Kaufman ............................ 606/34 |
| 5,413,575 | 5/1995 | Haenngi ............................ 606/45 |
| 5,431,650 | 7/1995 | Cosmescu .......................... 606/41 |
| 5,451,222 | 9/1995 | De Maagd et al. ................ 606/45 |
| 5,460,602 | 10/1995 | Shapira ............................. 604/22 |
| 5,613,966 | 3/1997 | Makower et al. .................. 606/34 |

OTHER PUBLICATIONS

"ClearCut 2™ Electrosurgical Handpiece," Medtronic, Inc., 1995.
"ProtectAire™ Smoke Evacuation Systems," Medtronic, Inc., 1995.

*Primary Examiner*—Jennifer Bahr
*Assistant Examiner*—Michael Peffley
*Attorney, Agent, or Firm*—Foley & Lardner

[57] ABSTRACT

A smoke reducing device for use in minimally invasive surgery includes a housing having an inlet opening from an outlet opening. The housing is sized to fit through a trocar opening that leads to a body cavity. A filter is positioned within the housing between the inlet and outlet openings. An air flow generator is located within the housing and is positioned to draw air in through the inlet opening, pulled through the filter, and exhausted through the outlet opening to draw any smoke created during minimally invasive surgery through the filter. The smoke reducing device may form part of an electrocautery device such that smoke created during minimally invasive surgery can be filtered internally of the body cavity.

18 Claims, 2 Drawing Sheets

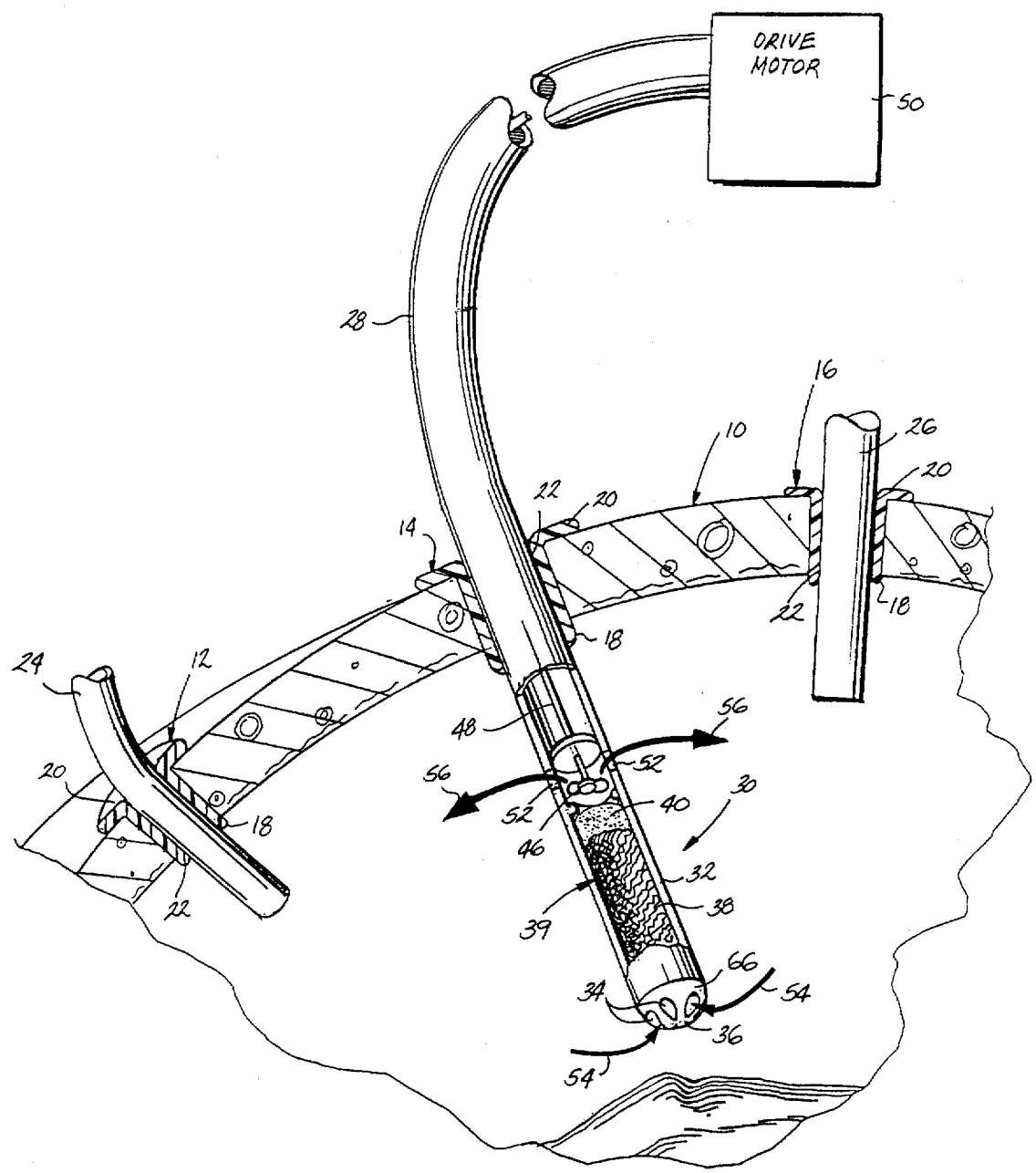
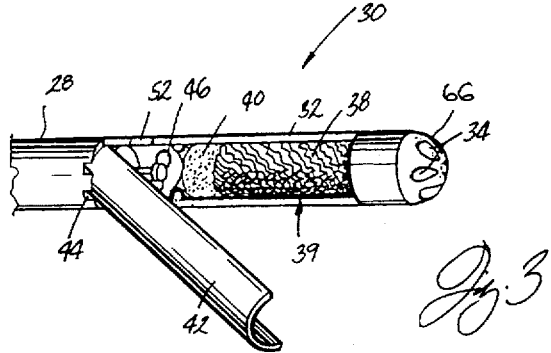

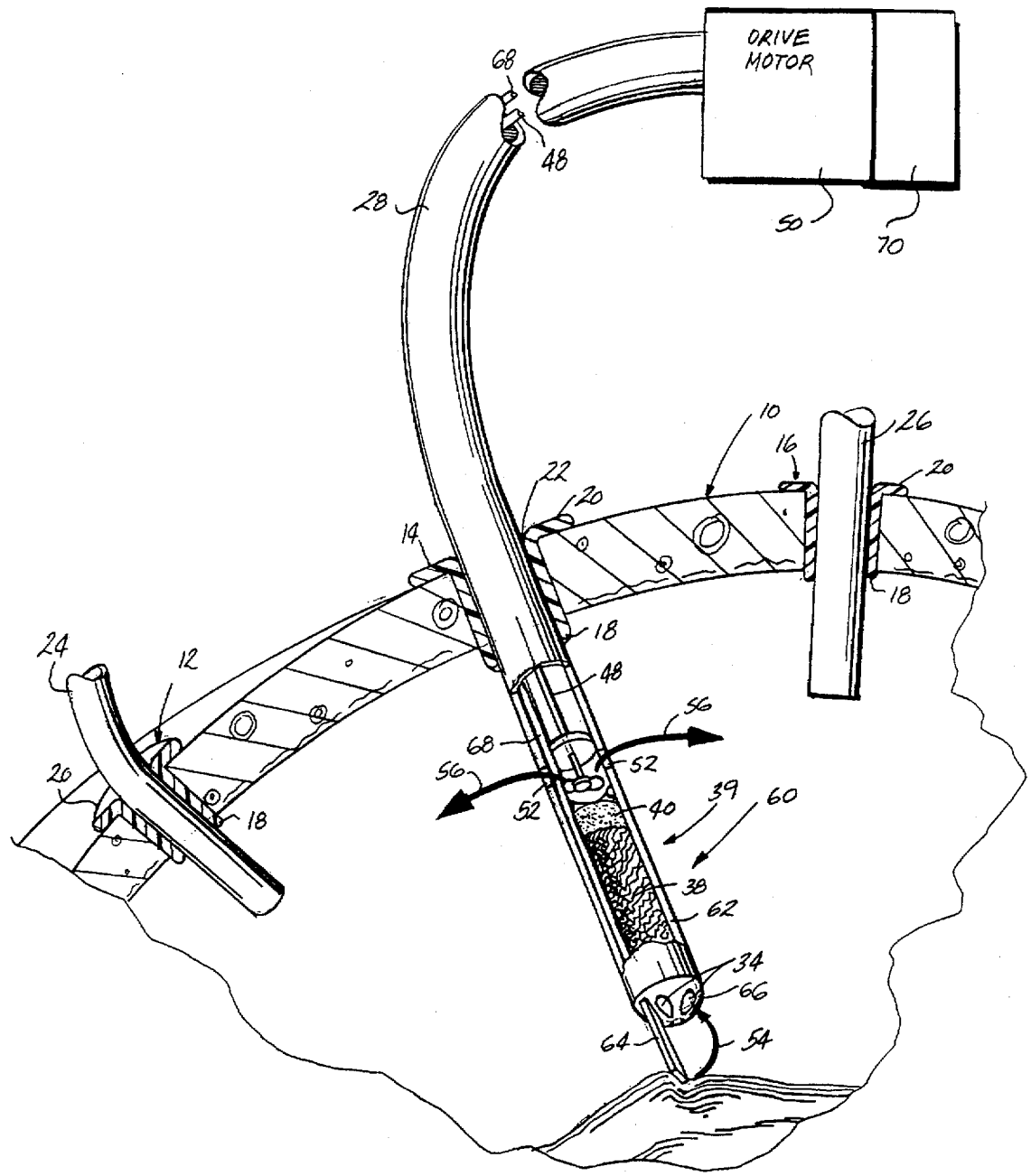

5,709,675

SMOKE REDUCING DEVICE FOR MINIMALLY INVASIVE SURGERY

BACKGROUND OF THE INVENTION

1. Field of the Invention

This invention relates to an instrument for use in laparoscopic or thoracoscopic surgical procedures, and more particularly to a smoke removal system for use during such procedures.

2. Description of the Related Art

In conventional laparoscopic procedures, several minimally-invasive surgery access ports are formed in the patient's abdomen. An insufflator is inserted into one of the ports. The insufflator injects a suitable gas such as carbon dioxide into the abdomen to expand the abdomen creating an air space or working air cavity around the organs on which the surgical operation is to be performed. With the abdomen distended, a hollow air space is created allowing the surgeon room to move the surgical tools and endoscope.

Electrocautery devices are often used during surgery. These devices have the undesirable effect of generating smoke in the distended cavity. Electrocautery devices are used to cut tissue and cauterize blood vessels inside the abdomen. Typically, the patient is positioned on an electrically-conductive plate and the electrocautery device has an electrode provided at the tip thereof. An open electrical circuit with sufficient potential is created between the base plate and the electrocautery device. An electrical are is created between the tissue and the electrocautery device to both cut and cauterize the tissue. The generated smoke will at least partially obscure the surgical field, thereby complicating the surgical procedure.

It is known to use one of the minimally invasive surgery working ports as a vent so that as the insufflator forces $CO_2$ into the working cavity, at least a portion of the working air and smoke is vented therefrom. This prior attempt to cure the problem of smoke within the abdomen is unacceptable because it requires the surgeon to balance the flow rate of $CO_2$ into the abdomen along with the flow rate of the gas out the working vent so that the abdomen will retain the distended state. In addition, this procedure is inadequate because the amount of smoke generated generally far exceeds the capacity of the insufflator and vent.

SUMMARY OF THE INVENTION

These and other problems of the prior art are overcome by the provision of a mechanism that is adapted to filter the air inside the working cavity. Preferably, the air is drawn through a filter mechanism and returned to the working cavity thereby not affecting the operation of the insufflator.

According to one aspect of the invention, the smoke reducing device for use in surgery includes a housing having an inlet opening spaced from an outlet opening. A filter is positioned within the housing between the inlet and outlet openings and an air flow generator is located within the housing. Preferably, the air flow generator is positioned proximate to the outlet opening to thereby filter any smoke generated during surgery.

In one embodiment of the invention, an electrode of an electrocautery device extends from an end of the housing to simultaneously allow cutting, cauterizing, and smoke reduction with the same tool.

According to another aspect of the invention, a smoke reducing device for use in minimally invasive surgery includes a housing having an inlet opening spaced from an outlet opening. The housing is sized to fit within a body cavity and preferably can be fit through a trocar opening that leads to the body cavity. A filter is adapted for positioning within the housing between the inlet and outlet openings. An air flow generator is located within the housing and is preferably positioned proximate to the outlet opening, so that smoke created during minimally invasive surgery can be filtered internally of the body cavity. The air flow generator is preferably a cable-driven fan (similar to the cable drive on known intravascular pumps). As the fan rotates, air is drawn in through the inlet, pulled through the filter, and exhausted through the outlet. The filter material can be formed of activated charcoal, polyester, fiber, or may be of the HEPA type. The device can be adapted for one use, and then discarded or the filter cartridge can be replaceable by providing a hinge along the smoke reducing housing so that the device can be used repeatedly.

With these arrangements, there is no need to balance the flow of pressurized air into the distended body cavity with the smoke reducing device because the filtering mechanism does not alter the pressure realized inside the cavity. In addition, the filter mechanism is far more effective in removing smoke from the surgical field than the processes known in the prior art.

BRIEF DESCRIPTION OF THE DRAWINGS

The invention will now be described with reference to the drawings in which:

FIG. 1 is a partial cross-sectional view of a distended body cavity with a smoke reducing device according to the present invention received therein;

FIG. 2 is a partial cross-sectional view of a distended body cavity showing a second embodiment of a smoke reducing system according to the present invention employing an electrocautery tip; and FIG. 3 is a partially enlarged view of FIG. 1 showing a hinged door for accessing a filter cartridge located within the smoke reducing device.

DETAILED DESCRIPTION OF THE PREFERRED EMBODIMENTS

In minimally invasive surgical procedures, such as in laprascopic surgery, multiple small incisions are made in the abdomen wall 10 of a patient for the receipt of surgical instruments. For example, three small incisions may be made in the abdomen wall 10 of a patient at different positions on the abdomen. A first trocar 12 is inserted into the first incision, a second trocar 16 is inserted into the second incision and a third trocar 14 is inserted into the third incision. Each trocar is conventional and has a boss 18 depending from a flange 20. The flange 20 is larger in diameter than boss 18, so that when the trocar is installed by pushing the boss through the incision, the flange will rest on the patient's outer epithelial layer. A central aperture 22 extends through each trocar for the reception of surgical instruments, tubes, etc. Once the trocars are installed, conventional devices such as an endoscope, a first surgical instrument, and a second surgical instrument, as represented generically by a first tube or cannula 24, a second tube or cannula 26, and a third tube or cannula 28, are inserted as needed into the central apertures of the several trocars. The number of incisions and trocars mounted in the patient and the particular surgical tools which are inserted are dependent entirely upon the surgical procedure being performed and are not specifically relevant to the invention.

A smoke reducing device 30 according to the present invention includes a hollow housing 32 attached to tube 28 in an air-tight arrangement. Air inlet openings 34 are preferably located at the distal end 36 of the housing 32. However, the inlet opening 34 can be provided at any point along the length of the device 30 which is received inside the body in the operative position. A first filter 38 is provided immediately adjacent the air inlet openings 34. The first filter 38 is preferably formed of an adsorb material, such as an activated charcoal material. However, other filter materials, such as polyester can be used. Moreover, the filter may be of the HEPA (high efficiency particulate) or fiber type. A second filter 40 may be provided to collect fines or particles that separate from the first filter 38. The second filter 40 is preferably of the absorb type. The first and second filters may be assembled together as a cartridge 39 during manufacturing. Alternatively, the first and second filters may be spaced from each other in housing 32 without affecting their operation. A door 42 is pivotably attached to the filter housing 32 through a hinge 44, as shown in FIG. 3. The door 42 permits access to the filter cartridge when open to permit its replacement. A substantially air-tight seal is preferably created between the housing and door when the door is closed.

An air flow generator, such as fan 46, is provided in proximity to the second filter, or in proximity to the first filter when only one filter is used. The fan 46 is preferably driven by a flexible cable assembly 48 and drive motor 50 in a manner similar to the intravascular pump as described in U.S. Pat. No. 4,817,586 issued on Apr. 4, 1989 to Wampler and U.S. Pat. No. 4,846,152 issued on Jul. 11, 1989 to Wampler et al., the disclosures of which are hereby incorporated by reference. The drive cable 48 extends through tube 28 between the drive motor 50 and fan 46. Alternatively, a small high speed motor (not shown) powered by a suitable battery or electrical leads extending through tube 28 can be positioned within the housing 32 and directly connected to the fan.

Air outlets 52 are provided around the periphery of the housing 32 immediately adjacent the fan 46. As the fan 46 rotates, air is drawn in through the inlet openings 34 as denoted by arrows 54, pulled through the filters 32 and 40, and exhausted through the outlet openings 52 as denoted by arrows 56 to draw any smoke created during minimally invasive surgery through the filter. Preferably, the air outlets 52 are positioned on the housing 32 so that the outlets 52 are received inside the distended body cavity when the device 30 is in the operative position. With this structure, the air flow is contained entirely within the body cavity, thereby eliminating the need to balance the flow rate of air into and out of the body cavity during the procedure. In an alternate arrangement, filters 38 and 40 may be reversed from that seen in FIG. 1, and the air drawn in through openings 52, pushed through the filters, and exhausted out of openings 34. The term "air" as used herein refers to any gas or gases that may be present, either inside or outside of the body cavity. An on/off switch (not shown) may be located remotely from the fan and interfaced between the fan drive unit and an electrical source to actuate the fan as needed.

The housing 32 is preferably formed of a stiff polymeric or stainless steel material that can be sterilized for multiple use. The stiff material permits the housing walls to remain in their original shape when subjected to any vacuum forces created by the fan. Alternatively, the filter cartridge may be of sufficient rigidity to permit a flexible housing material. The housing 32 and tube 28 may then be formed continuously from a single tube. The air inlets 34 and distal end 36 could be formed as part of the filter cartridge, to allow installation of the filter cartridge into an end of the tube.

In use, the smoke reducing device 30 is inserted through a trocar 14 and positioned in proximity to the electrode of an electrocautery device in the abdomen during laprascopic surgery. Any smoke generated by the electrode is quickly and efficiently filtered by drawing the air through the filter mechanism without leaving the abdomen. Since the filtering device does not alter the pressure realized inside the distended working cavity, there is no need to balance the flow of pressurized air in the distended cavity. This device may be used alone, or in combination with an insufflator and vent to permit an even greater amount of smoke removal when so required.

Referring now to FIG. 2, a combination smoke reducing and electrocautery device 60 according to a second embodiment of the invention is shown, wherein like numerals in the previous embodiment are used to identify like parts. The device 60 includes a housing 62 having an electrode 64 extending from the distal end 66 of the housing 62. A plurality of air inlet openings are preferably formed at the distal end 66. The electrode 64 is connected to a source of power 70 via an electrical wire 68 extending through the housing 62 and tube 28. The source of power 70 is also connected to an electrically-conductive plate (not shown) upon which a patient is positioned during surgery. An open electrical circuit with sufficient potential is created between the conductive plate and the electrode tip to generate an arc between the tissue and the electrode to both cut and cauterize the tissue.

As in the previous embodiment, a filter cartridge 39 comprising a first filter 38 and a second filter 40 can be provided in housing 62. Depending on the type of filter used, the second filter may be eliminated. A fan 46 is positioned in proximity to the second filter, or in proximity to the first filter when only one filter is used. Air outlet openings 52 are provided around the periphery of the housing 62 immediately adjacent the fan 46. As the fan 46 rotates, air is drawn in through the inlet openings 34 as denoted by arrows 54, pulled through the filters 32 and 40, and exhausted through the outlet openings 52 as denoted by arrows 56 to draw any smoke created during minimally invasive surgery through the filter. The proximity of the inlet openings 34 to the electrode 64 permits the reduction of smoke created by the electrode in a quick and efficient manner.

Reasonable variation and modification are possible within the spirit of the foregoing specification and drawings without departing from the scope of the invention.

The embodiments for which an exclusive property or privilege is claimed are defined as follows:

1. A smoke elimination device for use inside a body of a patient comprising:

a housing having a hollow interior, an air inlet port and an air outlet port, the inlet and outlet ports being in fluid communication with the hollow interior, the inlet and outlet ports being positioned so that both the ports are received inside the body when the device is in the operative position;

a first filter member positioned inside the hollow interior of the housing, intermediate the air inlet and outlet ports; and an air flow generator provided in the housing and adapted to draw air into the housing through the air inlet port, and force the air through the first filter member and the outlet port.

2. A smoke elimination device according to claim 1 wherein the air flow generator comprises a fan provided in the housing, adjacent the first filter member.

3. A smoke elimination device according to claim 2 wherein the fan is provided in the housing, downstream from the filter so that air is drawn through the filter.

4. A smoke elimination device according to claim 2 and further comprising a drive motor adapted to provide a motive means for the fan and a drive cable interconnecting the drive motor and the fan, the cable being adapted to conduct the motive means from the drive motor to the fan.

5. A smoke elimination device according to claim 1 and further comprising an electrocautery electrode extending from the housing, the electrode being adapted to cauterize and cut tissue inside the body.

6. A smoke elimination device according to claim 1 and further comprising a second filter member provided in the housing intermediate the air inlet and outlet ports.

7. A smoke elimination device according to claim 6 wherein the second filter member is formed from an absorbent material.

8. A smoke elimination device according to claim 6 wherein the first filter member is formed from an adsorbent material.

9. A smoke elimination device according to claim 1 wherein the first filter member is formed from an adsorbent material.

10. A smoke elimination device according to claim 1 and further comprising an access door provided on the housing and moveable between an operative position and an open position, in the open position, the door provides access to the hollow interior of the housing so that the first filter member can be removed therefrom.

11. A smoke elimination device according to claim 10 wherein the access door is pivotally mounted to the housing.

12. A method of reducing smoke inside a body during a surgical procedure comprising the steps of:

creating at least one incision in the skin of the body;

providing a smoke reduction device comprising:

a housing having a hollow interior, an air inlet port and an air outlet port, the inlet and outlet ports being in fluid communication with the hollow interior, the inlet and outlet ports being positioned so that both the ports are received inside the body when the device is in the operative position;

a first filter member positioned inside the hollow interior of the housing, intermediate the air inlet and outlet ports; and an air flow generator provided in the housing and adapted to draw air into the housing through the air inlet port, and force the air through the first filter member and the outlet port;

inserting the housing through one of said at least one incisions, the housing being inserted a sufficient distance so that the inlet and outlet ports are both positioned inside the body;

actuating the air flow generator so that air inside the body is drawn into the housing through the inlet port, through the filter member and exhausted from the housing through the outlet port.

13. A method of reducing smoke inside a body according to claim 12 and further comprising the step of providing an electrocautery electrode on the housing, the electrode being positioned so that the electrode is positioned inside the body when the device is in the operative position.

14. A method of reducing smoke inside a body according to claim 13 and further comprising the step of providing an access door on the housing for accessing the first filter member.

15. A method of reducing smoke inside a body according to claim 14 and further comprising the step of removing the first filter member when the filter member has become soiled and replacing the filter member with a clean filter member.

16. A method of reducing smoke inside a body according to claim 12 and further comprising the step of providing an access door on the housing for accessing the first filter member.

17. A method of reducing smoke inside a body according to claim 16 and further comprising the step of removing the first filter member when the filter member has become soiled and replacing the filter member with a clean filter member.

18. A method of reducing smoke inside a body according to claim 12 and further comprising the step of removing the first filter member when the filter member has become soiled and replacing the filter member with a clean filter member.

* * * * *